United States Patent [19]

Davies et al.

[11] Patent Number: 5,425,263
[45] Date of Patent: Jun. 20, 1995

[54] METHOD FOR INSPECTING AN ARTICLE FOR CONCEALED SUBSTANCES

[75] Inventors: John H. Davies, Port Credit; Frank J. Kuja, Brampton, both of Canada

[73] Assignee: Barringer Research Limited, Rexdale, Canada

[21] Appl. No.: 69,477

[22] Filed: Jun. 1, 1993

[51] Int. Cl.⁶ ............................................. G01N 25/14
[52] U.S. Cl. .................................... 73/28.05; 73/28.06
[58] Field of Search ................. 73/28.04, 28.05, 28.06

[56] References Cited

U.S. PATENT DOCUMENTS

| | | | |
|---|---|---|---|
| 3,088,364 | 5/1963 | Rozsa | 88/14 |
| 3,128,619 | 4/1964 | Lieberman | |
| 3,360,125 | 12/1967 | Horsey | 209/12 |
| 3,731,464 | 5/1973 | Brumbaugh | 55/270 |
| 3,759,617 | 9/1973 | Barringer | 356/36 |
| 3,768,302 | 10/1973 | Barringer | 73/28.01 |
| 3,868,222 | 2/1975 | Barringer | |
| 3,970,428 | 7/1976 | Barringer | |
| 3,972,225 | 8/1976 | Fort et al. | 73/28.04 |
| 3,985,619 | 10/1976 | Barringer | 195/103.5 R |
| 3,998,734 | 12/1976 | Barringer | 210/65 |
| 4,056,969 | 11/1977 | Barringer | 55/270 X |
| 4,192,176 | 3/1980 | Barringer | 73/28.04 |
| 4,251,356 | 2/1981 | Harte | 209/250 |
| 4,455,222 | 6/1984 | Less | 209/12 |
| 4,568,520 | 2/1986 | Ackermann | 422/66 |
| 4,767,524 | 8/1988 | Yeh | 209/143 |
| 4,972,957 | 11/1990 | Liu | 209/143 |
| 4,987,767 | 1/1991 | Corrigan et al. | 73/28.04 X |
| 5,128,539 | 7/1992 | Rodgers et al. | 73/28.05 X |

FOREIGN PATENT DOCUMENTS

| | | |
|---|---|---|
| 966766 | 4/1975 | Canada . |
| 974437 | 9/1975 | Canada . |
| 1132659 | 8/1982 | Canada . |
| 1377453 | 12/1974 | United Kingdom . |
| 498581 | 3/1976 | U.S.S.R. ............ 73/28.04 |

*Primary Examiner*—Thomas P. Noland
*Attorney, Agent, or Firm*—Bereskin & Parr

[57] ABSTRACT

There is provided an assembly for preferentially separating and collecting particles that are gathered from the surface of an article such as an item of baggage. The assembly features an impactor and a suction anvil that is displaceable from a collection medium. The anvil is displaceable from the collection medium so that the medium may be removed and analyzed for traces of substances such as explosives or narcotics. There is also provided, in combination with the assembly, a vacuum head and conduit for gathering the particles and a suction unit for creating the suction force. The collection medium containing collected particles is moved from the impactor to an analyzer by a stage movement device. The analyzer includes an analysis unit, such as an Ion Mobility Spectrometer, and a displaceable heater anvil.

4 Claims, 4 Drawing Sheets

METHOD FOR INSPECTING AN ARTICLE FOR CONCEALED SUBSTANCES

FIELD OF THE INVENTION

The present invention relates to the field of aerosol separators and particle detection apparati. In particular the invention provides an assembly for separating and collecting particles of a minimum desired size from a main, particle-laden airflow. The invention further provides an apparatus incorporating the above-identified assembly for inspecting articles for concealed substances, such as narcotics and explosives.

BACKGROUND OF THE INVENTION

Devices that separate or concentrate particles from an airflow and direct them to a collection medium are known. Examples of such devices are provided in U.S. Pat. Nos. 3,731,464 (Brumbaugh et al.); 4,767,524 (Yeh et al.); and 4,972,957 (Liu et al.).

Such conventional aerosol selection devices separate the particle laden air into two airflows by inertial separation. The larger sized particles are then conducted to a collector that is located externally to the selection device. None of the prior art devices enable the selection and collection to be accomplished in a single simple assembly.

U.S. Pat. No. 4,972,957 attempts to provide such an assembly by including impactor plates within the selector that collect the separated particles. It is still necessary to partially disassemble the apparatus however, in order to remove the impactor plates for their subsequent analysis. It is preferable that the separation, collection and analysis be accomplished in an efficient manner so that subsequent air flows may be analyzed in quick succession.

While it has always been desirable to provide a simplified separation and collection assembly, the need for such an assembly has been highlighted by recent developments in the area of concealed substance detection.

Conventional detection techniques involve the collection of vapors that are emitted from concealed substances and the subsequent identification of such vapors using mass spectrometric, chromatographic, or chemiluminescent techniques. The lower vapor pressures of modern plastic explosives and narcotics such as cocaine or heroin, make their detection by vapor collection very difficult, if not impossible.

Recent developments in the field of contraband detection have been directed toward the analysis of particles that attach themselves to articles such as baggage. Particles of explosives and narcotics are transferred to the surface of these articles by persons who have been handling said explosives and narcotics. It is also recognized that substances having lower vapor pressures nevertheless emit trace amounts of vapor that will agglomerate with dust or other particles that settle upon articles or are transferred to such articles by persons handling the substances. Such particles may be vacuumed from the article and the particles may be collected upon a collection medium. The collection medium may then be heated to release the vapors agglomerated upon the particles collected. The vapors may then be analyzed by mass spectrometry or other techniques to determine their chemical makeup.

One problem faced with such detection techniques is the occurrence of false alarms caused by an abundance of small particles introduced to the collection medium. These may be caused by a general level of contamination by a particular substance, ie. a background effect, rather than being indicative of the presence of a significant quantity of the substance. It has now been discovered that any background effect or incidental contamination will be caused by relatively small particles. If there is any significant quantity of a substance of interest, then it should give off larger particles. Thus, it has now been discovered that by preferentially collecting only larger particles, erroneous readings due to background effects are substantially eliminated. It is therefore desirable that a concealed substance detection apparatus include a particle selector for selecting particles of a desired size.

As previously discussed, conventional particle selectors are not adaptable to large scale detection applications because of their failure to provide a single simple assembly for the selection and collection of particles. Such an assembly is desired in order that articles may be examined in relatively quick succession. To accomplish this, it is necessary that the collection medium be quickly accessed or moved from the collection location to an analysis location.

The present invention therefore provides an assembly for selecting and collecting particles, as well as an apparatus incorporating such an assembly for enabling the analysis of particles in an efficient manner.

SUMMARY OF THE INVENTION

In one aspect of the invention there is provided a method for inspecting an article for concealed substances, by collection and analysis of particles carried by the article, said method comprising the following steps:

(a) collecting particles from the article and entraining them into a main airflow;

(b) separating the main airflow in an impactor into a first airflow depleted in the particles and a second airflow into which the particles are preferentially concentrated;

(c) causing the second airflow to pass through a collection medium, in which the particles are collected, said collection medium being displaceably held against said impactor by a suction anvil;

(d) transferring the collection medium to an analysis unit which includes an analyzer, and heating the collection medium to vaporize the particles and entraining the vapor with a gas flow into the analyzer said collection medium being displaceably held against an inlet to said analyzer by a heater anvil.

In another aspect of the invention there is provided a method for inspecting an article for concealed substances by the collection and analysis of particles carried by the article, said method comprising the following steps:

(a) activating a power switch at a vacuum head to cause a suction anvil displacement unit and a heater anvil displacement unit to respectively displace a suction anvil and a heater anvil from a rest position to an operational position;

(b) sensing when such suction and heater anvils are in their operational position and consequently engaging a suction force at said vacuum head to remove particles from said article into a main airflow;

(c) introducing said main airflow to an inlet of an assembly for separating and collecting particles of a desired size, said assembly having an impactor, said displaceable suction anvil, said suction anvil displacement unit, and a collection medium situated between said impactor and said suction anvil, wherein particles of a desired size are preferentially separated from the main airflow and are collected by the collection medium;

(d) deactivating said power switch at said vacuum head to disengage said suction force and to cause said suction anvil displacement unit and said heater anvil displacement unit to respectfully displace said suction and heater anvils from said operational position to said rest position;

(e) sensing when said suction and heater anvils are in their rest position and consequently engaging a takeup motor of a stage movement device to move said collection medium containing collected particles to an analyzer, said analyzer having an analysis unit, said displaceable heater anvil, and said heater anvil displacement unit, wherein said collection medium containing said collected particles becomes situated between said analyzer unit and said heater anvil, and wherein said heater anvil heats said collection medium to release vapors from said collected particles into said analyzer for subsequent analysis;

wherein said collection and analysis of particles occurs simultaneously and wherein the steps may be repeated to inspect further articles.

Further objects and advantages of the invention will appear from the following description, taken together with the accompanying drawings.

BRIEF DESCRIPTION OF THE DRAWINGS

For a better understanding of the present invention, and to show more clearly how it may be carried into effect, reference will now be made, by way of example, to the accompanying drawings, which show a preferred embodiment of the present invention, and in which.

DESCRIPTION OF THE PREFERRED EMBODIMENT

Reference is first made to FIGS. 1 to 4 which show an assembly 10 for separating and collecting particles of a desired minimum size from a main particle laden airflow generally indicated as A+B.

The assembly 10 includes a particle separator that has an impactor 12, a displaceable suction anvil 14, and a collection medium 15 located therebetween.

Figure 1:
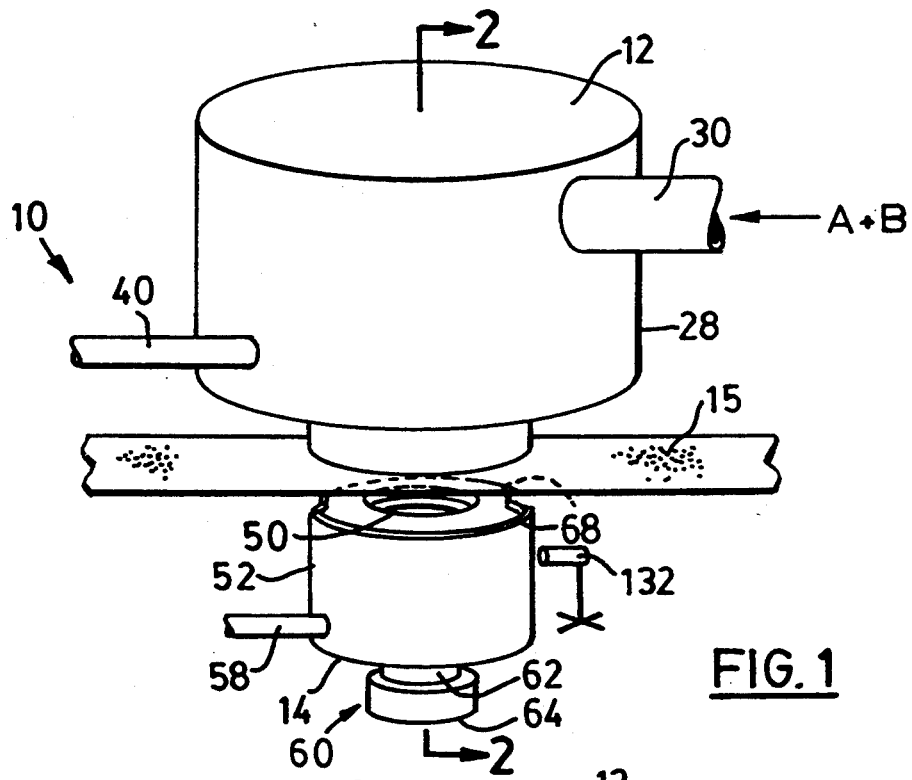
FIG. 1 is a perspective view of an assembly for separating and collecting particles of a minimum desired size from a main particle laden airflow.
Figure 2:
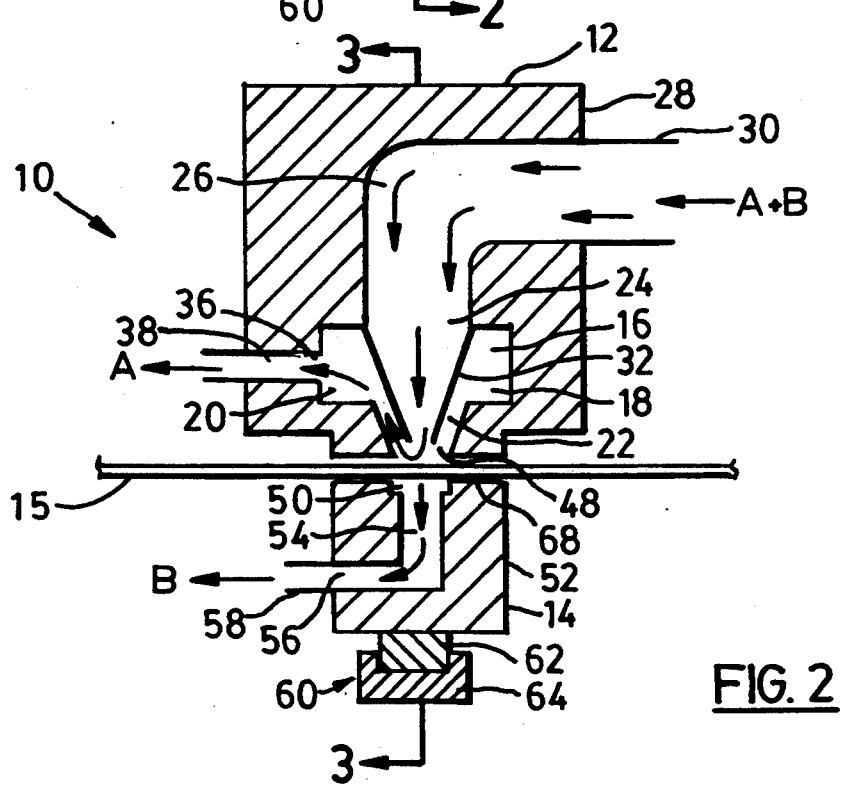
FIG. 2 is a sectional view of the assembly shown in FIG. 1 along lines 2—2.
Figure 3:
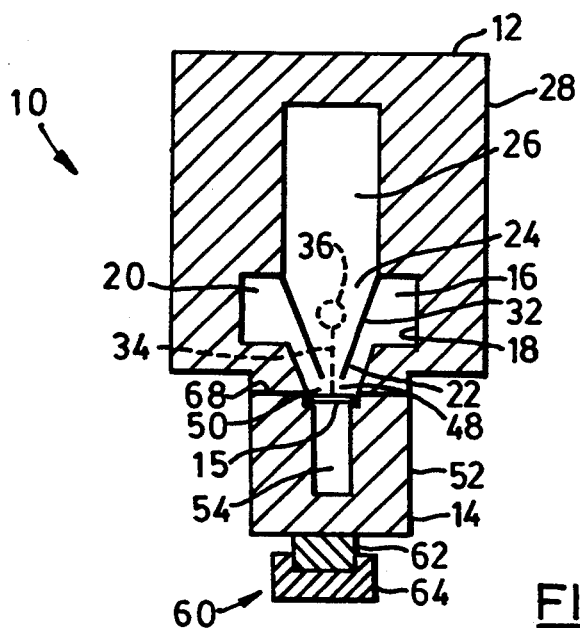
FIG. 3 is a sectional view of the assembly shown in FIG. 2 along lines 3—3.
Figure 4:
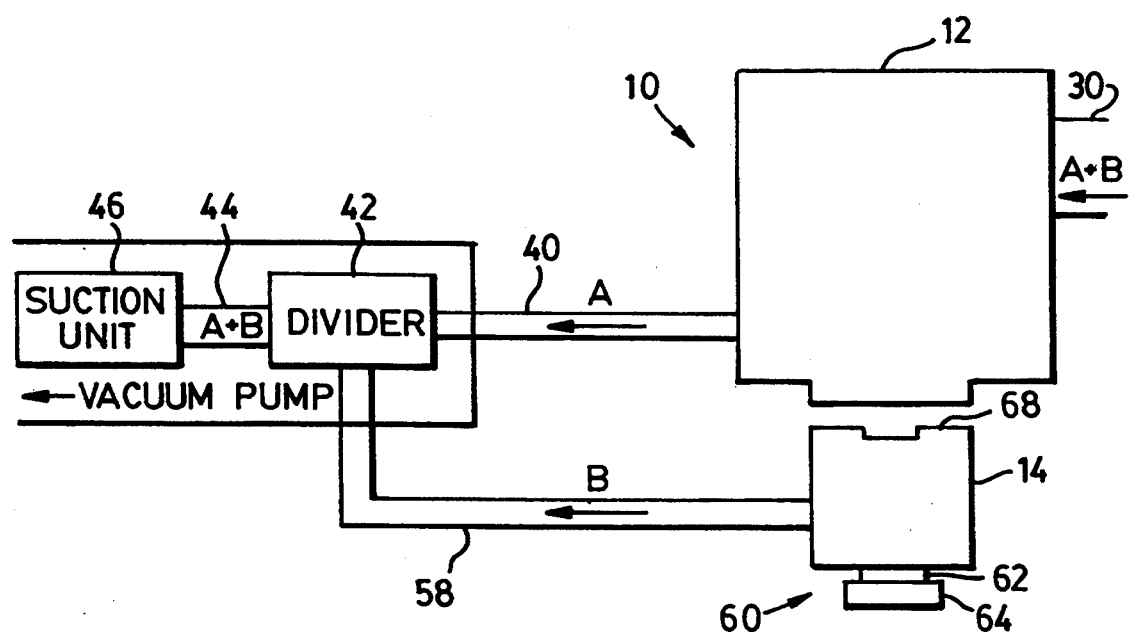
FIG. 4 is a schematic diagram showing an assembly according to FIGS. 1 to 3 and further depicting its connection to a suction unit and divider.

The impactor 12 has a cavity 16 that is enclosed by an internal wall 18 of the impactor body. As shown in FIG. 2, the cavity 16 has first and second regions 20 and 22. The first region 20 is generally cylindrical and the second region 22 is generally frusto-conical. An inlet 24 is provided within the wall 18 of the cavity 16 to allow ingress of the main airflow A+B. The inlet 24 is connected to an inlet channel 26 within the impactor 12 leading to the exterior wall 28 of the impactor 12. At this point the channel 26 may be connected to a conduit 30 leading from the sampling area where the main airflow A+B is gathered.

The inlet 24 has a nozzle 32 extending from it into the cavity 16. The nozzle 32 is preferably frusto-conical in shape and extends a substantial distance into the second region 22 of the cavity 16. A reverse flow passage is thus defined between the frusto-conical nozzle 32 and frusto-conical second region 22. As shown, this reverse flow passage has a generally uniform radial extent, and extends back to the cylindrical first region.

The main airflow A+B is introduced to the cavity 16 along a main axis 34 as indicated by the dashed line in FIG. 3. The nozzle 32 is generally concentric about this axis 34 as are the first and second regions 20 and 22 of the cavity 16.

A first opening 36 is defined within the wall 18 of the first region 20 of the cavity 16 at a position perpendicular to the axis 34. This opening is connected to a first flow channel 38 leading to the exterior wall 28 of the impactor 12. At this point the channel 38 may be connected to a first flow conduit 40 leading to a divider 42 as is shown in FIG. 4. The divider 42 is connected by a conduit 44 to a suction unit 46.

A second opening 48 is defined within the wall 18 of the second region 22 of the cavity 16 at a position coincident with the axis 34. This opening is cooperable with an anvil inlet opening 50 defined within the exterior wall 52 of the suction anvil 14 described further below. A second flow channel 54 leads from the anvil inlet opening 50 through the anvil to an anvil outlet opening 56 on the exterior wall 52 of the suction unit 46. At this point the channel 54 may be connected to a second flow conduit 58 leading to the divider 42.

The suction provided by the suction unit 46 is represented as A+B in FIG. 4. A suction force of 100 in. $H_2O$. is considered sufficient for use in separating and collecting particles having a minimum desired size of 5 microns.

The suction A+B provided by the suction unit 46 is split into a first airflow A and a second airflow B by the divider 42 in a known manner. The first airflow A is connected by the first airflow conduit 40 and the first flow channel 38 to the first opening 36 in order to draw air and smaller sized particles from the first region 20 of the cavity 16. The draw is perpendicular to the axis 34 and thus perpendicular to the direction of the main airflow A+B exiting the nozzle 32.

The second airflow B is adjusted at the divider 42 to be about 5 to 25 percent of the first airflow A. The second airflow is connected by the second flow conduit 58 and the second flow channel 54 to the anvil inlet opening 50. When the suction anvil 14 is displaced to a position where the anvil inlet opening 50 is adjacent to the second opening 48 of the impactor 12 (as will be described further below), the second airflow B will draw larger sized particles against the collection medium 15 where they may be collected. The collection medium 15 must be porous in order to allow such a draw, and to allow particles to become embedded within the medium.

The displacement of the suction anvil 14 may be accomplished in a range of ways. Manual displacement through a simple mechanical displacement unit (not shown) may be utilized. Alternatively, if the assembly 10 is to be used for the analysis of different airflows in quick succession, it is preferable that an automatic displacement unit be utilized. A preferred automatic suction anvil displacement unit 60 would include a piston 62 that is raised and lowered by pneumatic, hydraulic or electromagnetic means 64. The piston 62 is raised and lowered according to control signals provided by a control unit 66 as is described further below.

Regardless of its configuration, the displacement unit 60 enables the suction anvil 14 to be moved from a "rest position" where the anvil inlet opening 50 is displaced from the impactor 12, to an "operational position" where the anvil inlet opening 50 is immediately adjacent the second opening 48 of the impactor 12, with the collection medium 15 therebetween.

The suction anvil 14 includes shoulders 68 that contact the impactor 12 to provide a substantially airtight seal about the anvil inlet opening 50 and second opening 48 when the anvil is in its operational position. FIG. 13 depicts the anvil in the operational position with the shoulders 68 in contact with the impactor 12. It should be understood that the seal will not be completely airtight when a continuous collection medium 15, such as a porous tape, is used. In such cases, the second airflow B must be increased so that the appropriate ratio of first and second airflows is obtained within the cavity 16.

The separator thus operates on the basis of inertial separation. A main airflow A+B enters the cavity 16 through the nozzle 32 along the axis 34 that is coincident with the second opening 48. The main airflow, upon exiting the nozzle 32, is subjected to a draw A created by the first airflow. In the preferred embodiment, the nozzle 32 extends into the second region 22 of a cavity 16 and the first airflow A is drawn from the first region 20 of the cavity 16. Many of the particles exiting the nozzle 32, generally the smaller and lighter particles, are thus drawn in a direction that is generally opposite to the particles' initial direction of travel. This is illustrated by arrows in FIG. 2. The draw A is strong enough to carry the air molecules and the smaller particles towards the first opening 36. Only particles having a sufficient inertia to overcome the draw A will succeed in passing through the cavity 16 toward the second opening 48, which generally will be the larger and heavier particles. Those particles passing through the second opening 48 will encounter the collection medium 15 and will be embedded within it by the second airflow B.

Any particles that fail to become embedded within the collection medium 15 will once again be drawn toward the first opening 36 by the first airflow A. The assembly 10 will therefore only collect those particles which have a desired minimum size and which become embedded within the collection medium 15.

The nozzle 32 is suitably dimensioned with respect to its angle of taper, exit diameter and height above the collection medium 15 to ensure the efficient transfer of particles into the collection medium 15, while at the same time removing air molecules and smaller particles. The volume of the cavity 16 and the ratio of airflows is also important. By varying the dimensions of the nozzle 32, the volume of the cavity 16, the ratio of flow rates, and the porosity of the collection medium 15, the minimum size of collected particles may be varied according to operational needs.

In order to collect particles having a minimum size of 5 microns, the assembly 10 is dimensioned as follows:
first airflow A: 160 liters/min
second airflow B: 40 liters/min
diameter of first region 20: 0.75 inches
diameter of second region 22—top: 0.50 inches
 bottom (second opening 48): 0.375 inches
height of first region 20: 0.25 inches
height of second region 22: 0.26 inches
diameter of inlet 24: 0.50 inches
exit diameter of nozzle 32: 0.25 inches
length of nozzle 32: 0.45 inches
diameter of first opening 36: 0.25 inches
porosity of collection medium 15: $8\mu$

APPARATUS INCORPORATING ASSEMBLY

Figure 5:
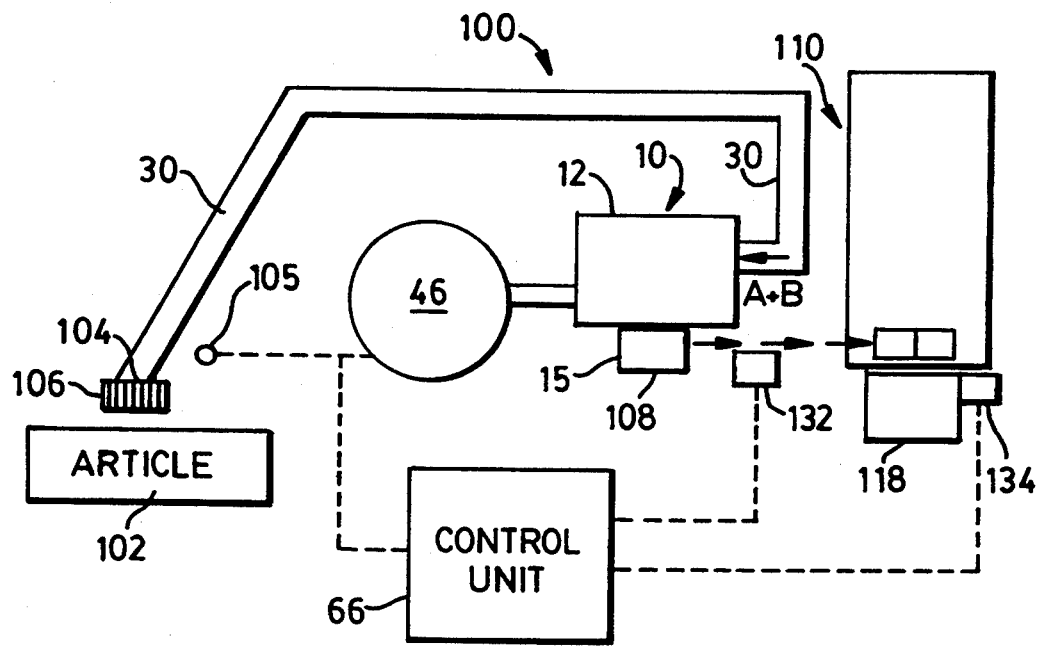
FIG. 5 is a schematic diagram of an apparatus for inspecting articles for concealed substances, such as narcotics or explosives.
Figure 6:
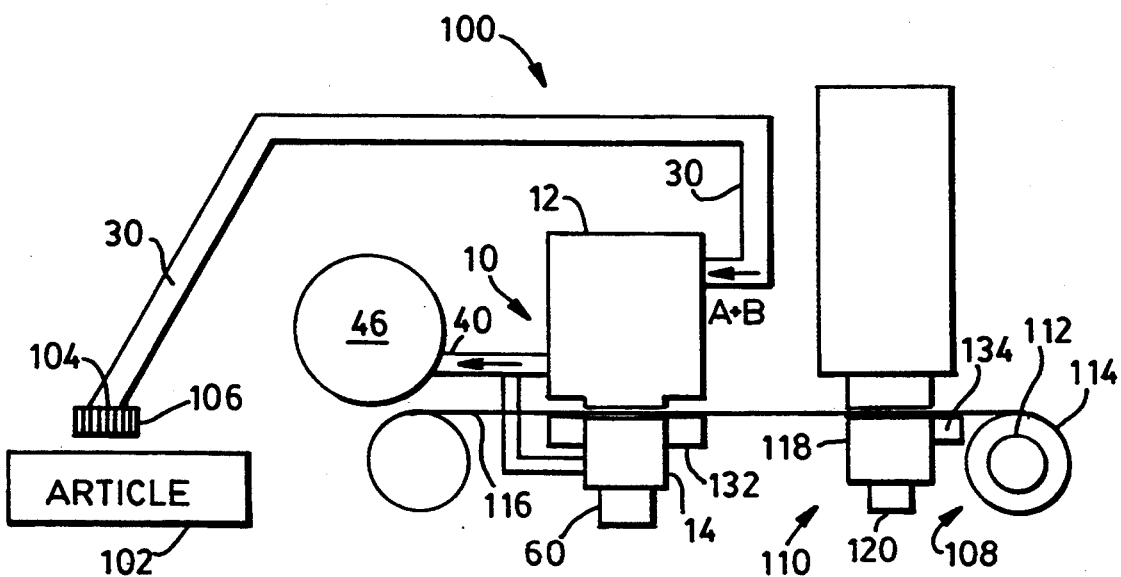
FIG. 6 is a schematic diagram of the apparatus showing a continuous tape collection medium and a stage movement device having a takeup motor and reel.

Reference will now be made to FIGS. 5 and 6 which each schematically depict an apparatus 100 that incorporates the above described assembly 10 for inspecting articles, such as baggage, for concealed substances. Those elements of the apparatus that correspond to similar elements of the above described assembly 10 will be given the same reference numerals, for ease of understanding.

The article to be inspected is schematically represented as 102. The apparatus contemplates the inspection of articles 102 such as baggage at an airport-type security setting. It is conceivable however that any form of article 102 may be inspected for traces of vapors emitted from substances such as narcotics or explosives. For instance, an individual's clothing may be inspected to identify whether the person was recently in contact with such substances.

The inspection of the article 102 may be accomplished with a vacuum head 104 which may include a brush 106 or other means for encouraging the removal of particles from the article 102. The suction at the vacuum head 104 is provided by the suction unit 46 described earlier. A power switch 105 is provided at the vacuum head 104 to operate the suction unit 46 at desired intervals.

The vacuum head 104 is attachable to the conduit 30 that conducts the main particle laden airflow A+B to the impactor 12 of the assembly 10.

The elements of the assembly 10, including the impactor 12, suction anvil 14, suction anvil displacement unit 60 and collection medium 15, are as described above and shown in FIGS. 1 to 4.

The apparatus further includes a stage movement device 108 for moving a portion of the collection medium 15 from a collection area adjacent the assembly 10, to an analysis area adjacent an analyzer 110. The operation of the stage movement device 108 is controlled automatically by the control unit 66, described further below.

In one embodiment as shown in FIG. 6, the stage movement device 108 includes a takeup motor 112 that advances a reel 114 containing the collection medium in the form of a tape 116. In another embodiment, the collection medium may be in the form of a discrete disk (not shown) situated upon a rotary table (not shown). The stage movement device 108 would then include a rotary motor for rotationally advancing the collection medium 15.

The analyzer 110 preferred for use with the present invention is an ion mobility spectrometer (IMS). Other types of analyzers may also be used, such as chromatography and chemilumiscent detectors.

Figure 7:
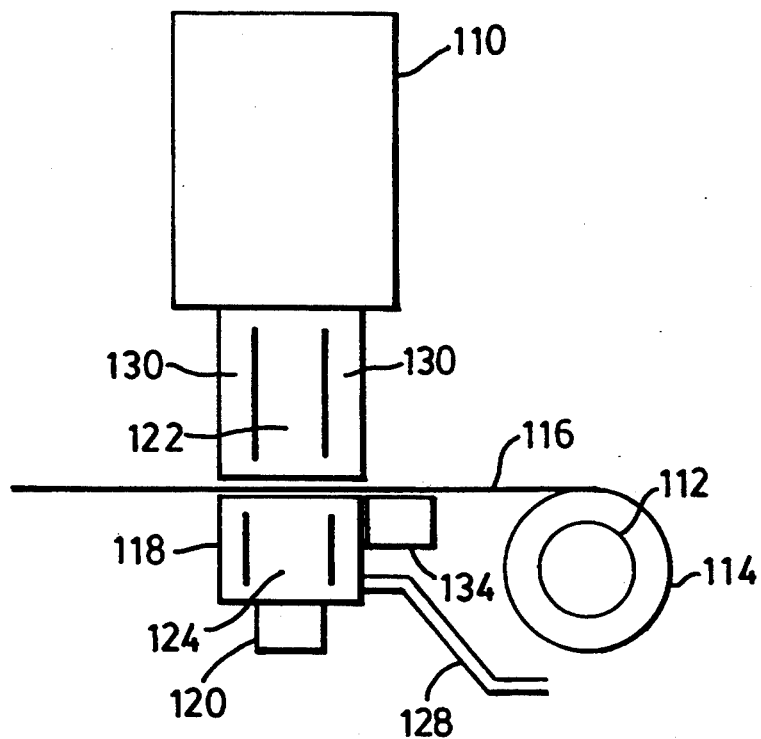
FIG. 7 is a schematic diagram of an analyzer and displaceable heating unit for analysing collected particles.

As is best seen in FIG. 7, the analyzer 110 includes a displaceable heater anvil 118 that is moved by a heater anvil displacement unit 120 similar to the suction anvil displacement unit 60 described above. The heater anvil 118 is moved by the displacement unit 120 from a rest position displaced from an analyzer inlet 122, to an operational position adjacent the analyzer inlet 122, with the collection medium 116 located therebetween. The heater anvil 118 includes a heater 124, such as a pyrolyser or thermal oven, that is in close proximity to or in direct contact with the collection medium 116 in order to heat the collected particles to release the accumulated vapors into the inlet 122 of the analyzer 110. A sample gas flow G, such as clean air or an inert gas, may be introduced by an airflow channel 128 through the heater anvil 118 to direct the desorbed vapors into the analyzer inlet 122. To ensure that the desorbed vapors do not subsequently condense while passing along the inlet 122 to the analyzer 110, an inlet heater 130 is provided.

It is important that the particles are firmly embedded within the collection medium 116 and are not released when the heater 124 or gas flow G is activated. Only the vapors that have accumulated upon the particles should be released by the heating operation. The release of particles into the IMS analyzer would affect the results achieved as well as endanger the operation of the analyzer 110.

The operation of the IMS analyzer itself is known and will not be described herein. Examples of such devices are provided in U.S. Pat. Nos. 4,311,669 and 4,551,624 by Glenn E. Spangler.

CONTROL UNIT

The automatic operation of the apparatus is controlled through the control unit 66. The control unit 66 receives input information from the vacuum head power switch 105 and from sensors located at the suction and heater anvils.

The suction anvil sensor 132 and the heater anvil sensor 134 each sense when their respective anvils are in the operational positions. These sensors may be in the form of mechanical microswitches or proximity sensors. The present invention contemplates the use of microswitches.

The control unit 66 receives input from the sensors and accordingly controls the operation of the displacement units 60 and 120, the takeup motor 112, and the heater 124.

The control unit 66 controls the apparatus 100 as follows. At the outset, it should be assumed that the respective displacement units 60 and 120 are in a rest position and that an unused portion of the collection medium 15 is situated in a collection area and a used portion of the collection medium 15 containing collected particles is located in the analysing area. When the power switch 105 at the vacuum head 104 is activated, the control unit 66 directs the respective displacement units 60 and 120 to move the anvils 14 and 118 to their operational positions. When the respective microswitches sense that the anvils are in their operational positions, the control unit 66 activates the suction unit 46 and heater 124. When the power at the vacuum head 104 is switched off, the control unit 66 directs the respective displacement units 60 and 120 to move the anvils to a rest position. When the microswitches sense that the anvils are no longer in an operational position, the control unit 66 activates the takeup motor 112 (or rotary motor) to advance the collection medium 15. The apparatus is then once again in a position to collect a fresh sample and analyze the previously collected sample.

The above collection/analysis time, defined by the period between activation and deactivation of the power switch 105, may be varied by the operator or maintained at a fixed, pre-determined value. In the preferred embodiment with an IMS analyzer, the said collection/analysis time is greater than or equal to the IMS analysis time of typically six seconds. The control unit may deactivate the analyzer heater 124 if the collection/analysis time is significantly greater than six seconds.

It is understood that preferred embodiments of the invention have been described and that changes and alternative embodiments may be made within the spirit of the invention as defined by the appended claims.

We claim:

1. A method for inspecting an article for concealed substances, by collection and analysis of particles carried by the article, said method comprising the following steps:
   (a) collecting particles from the article and entraining them into a main airflow;
   (b) separating the main airflow in an impactor into a first airflow depleted in the particles and a second airflow into which the particles are preferentially concentrated;
   (c) causing the second airflow to pass through a collection medium in which the particles are collected, said collection medium being displaceably held against said impactor by a suction anvil; and
   (d) transferring said collection medium to an analysis unit which includes an analyzer, said collection medium being displaceably held against an inlet to said analyzer by a heater anvil, and heating the collection medium to vaporize the particles and entraining the vapor with a gas flow into the analyzer.

2. A method as claimed in 1, wherein the suction anvil and the heater anvil are operated simultaneously, whereby they are both held together in an operational position against the impactor and the analyzer respectively, and simultaneously withdrawn therefrom to rest positions spaced from the impactor and the analyzer, and wherein the transferral of the collection medium to the analysis unit in step (d) is effected with the suction and heater anvils in their rest positions and includes transferring a used collection medium away from the analyzer.

3. A method as claimed in claim 2, wherein step (a) is commenced when both the suction and heater anvils have been brought to their operational positions, with step (a) being effected for a predetermined length of time, following which the suction and heater anvils are displaced to their rest positions, wherein step (d) then comprises simultaneously transferring a collection medium from the impactor to the analyzer, discharging a used collection medium from the analyzer and transferring a fresh collection medium to the impactor, following which the suction and heater anvils return to their operational positions for commencement of a new cycle.

4. A method for inspecting an article for concealed substances, by the collection and analysis of particles carried by the article, said method comprising the following steps:

(a) activating a power switch at a vacuum head to cause a suction anvil displacement unit and a heater anvil displacement unit to respectively displace a suction anvil and a heater anvil from a rest position to an operational position;

(b) sensing when such suction and heater anvils are in their operational position and consequently engaging a suction force at said vacuum head to remove particles from said article into a main airflow;

(c) introducing said main airflow to an inlet of an assembly for separating and collecting particles of a desired size, said assembly having an impactor, said displaceable suction anvil, said suction anvil displacement unit, and a collection medium situated between said impactor and said suction anvil, wherein particles of a desired size are preferentially separated from the main airflow and are collected by the collection medium;

(d) deactivating said power switch at said vacuum head to disengage said suction force and to cause said suction anvil displacement unit and said heater anvil displacement unit to respectfully displace said suction and heater anvils from said operational position to said rest position;

(e) sensing when said suction and heater anvils are in their rest position and consequently engaging a takeup motor of a stage movement device to move said collection medium containing collected particles to an analyzer, said analyzer having an analysis unit, said displaceable heater anvil, and said heater anvil displacement unit, wherein said collection medium containing said collected particles becomes situated between said analyzer unit and said heater anvil, and wherein said heater anvil, on being displaced from a rest to an operational position as in step (a) above, heats said collection medium to release vapors from said collected particles into said analyzer for subsequent analysis;

wherein said collection and analysis of particles occurs simultaneously and wherein the steps may be repeated to inspect further articles.

* * * * *